United States Patent [19]

Hughes et al.

[11] 4,106,920

[45] Aug. 15, 1978

[54] METHOD OF MAKING A SEMI-PERMEABLE, ESSENTIALLY WATER-INSOLUBLE, HYDROPHILIC NYLON MEMBRANE AND RESULTANT PRODUCT

[75] Inventors: Robert D. Hughes; Edward F. Steigelmann, both of Park Forest, Ill.

[73] Assignee: Standard Oil Company (Indiana), Chicago, Ill.

[21] Appl. No.: 497,510

[22] Filed: Aug. 14, 1974

Related U.S. Application Data

[62] Division of Ser. No. 339,975, Mar. 12, 1973, Pat. No. 3,864,418.

[51] Int. Cl.$^2$ ................... B01D 59/10; B29D 27/04
[52] U.S. Cl. ........................ 55/158; 55/16; 264/49; 264/DIG. 62; 521/61
[58] Field of Search .............. 264/49, 41, DIG. 62; 55/16, 158, 90; 260/677 A, 679 A, 2.5 M

[56] References Cited

U.S. PATENT DOCUMENTS

| | | | |
|---|---|---|---|
| 2,846,727 | 8/1958 | Bechtold | 264/49 |
| 3,228,877 | 1/1966 | Mahon | 264/184 X |
| 3,276,996 | 10/1966 | Lazare | 264/49 X |
| 3,332,894 | 7/1967 | Cantor et al. | 264/41 X |
| 3,520,960 | 7/1970 | Douglas | 264/49 |
| 3,542,908 | 11/1970 | Sharples et al. | 264/49 |
| 3,711,583 | 1/1973 | Sklar | 264/49 |
| 3,719,590 | 3/1973 | Li et al. | 260/677 A X |
| 3,758,605 | 9/1973 | Hughes et al. | 260/679 A X |
| 3,770,842 | 11/1973 | Steigelmann et al. | 55/16 X |
| 3,878,109 | 4/1975 | Ikeda et al. | 254/41 X |
| 3,899,309 | 8/1975 | Hoehn et al. | 55/16 |

*Primary Examiner*—Philip Anderson
*Attorney, Agent, or Firm*—Bernard & Brown

[57] ABSTRACT

There is described the preparation of hydrophilic, semipermeable film membranes having an increase in pores and containing complex-forming metals. The films can be formed from solutions having film-forming material and pore-forming material dissolved in a solvent. The films can be useful for separating a component, e.g. an aliphatically-unsaturated hydrocarbon, from mixtures by the combined use of liquid barrier permeation and metal complexing techniques. The liquid barrier is at least partially within the hydrophilic film membrane during use, and the barrier contains complex-forming metal ions in aqueous solution. The metal ions may be, for example, noble metal, nickel, mercurous, cuprous or other metal ions, and mixtures of these metal ions, and the aqueous solution may contain other cations. The separation of ethylene from ethane and methane is of particular interest.

8 Claims, No Drawings

METHOD OF MAKING A SEMI-PERMEABLE, ESSENTIALLY WATER-INSOLUBLE, HYDROPHILIC NYLON MEMBRANE AND RESULTANT PRODUCT

This is a division of application Ser. No. 339,975, filed Mar. 12, 1973, now U.S. Pat. No. 3,864,418.

This invention relates to hydrophilic, semi-permeable film membranes containing complex-forming metals and having an increase in pores, but yet the membranes are essentially impermeable to liquids during use. These films can be made from solutions having the film-forming material and pore-forming material dissolved in a liquid solvent medium. The invention is also directed to the composited metal-containing membranes in both dry and aqueous forms. The films are useful for separating materials, e.g. aliphatically-unsaturated hydrocarbons, from mixtures containing the component to be separated along with other materials. The separation is performed by the combined use of liquid barrier permeation and metal complexing techniques wherein the liquid barrier containing complex-forming metal ions in aqueous solution is at least partially within the semi-permeable membrane. The films are especially useful for separating ethylene from gaseous mixtures containing it, other hydrocarbons, for example, one or both of ethane and methane, and with or without hydrogen.

There is considerable commercial interest in separating aliphatically-unsaturated hydrocarbons from mixtures containing them. These aliphatically-unsaturated hydrocarbons are reactive materials that serve in various roles, generally as intermediates in chemical syntheses. A number of the unsaturated hydrocarbons are employed as monomers in the formation of polymers and, in this regard, olefins such as ethylene, propylene, butadiene and isoprene are well known. These olefins, as well as other unsaturated materials, for instance, acetylene, are also used to form relatively low molecular weight products.

The aliphatically-unsaturated hydrocarbons are most often made available on a commercial basis in admixture with other chemical compounds, frequently other hydrocarbons. These unsaturated hydrocarbon-containing streams are usually by-products of chemical syntheses or separation processes. When the hydrocarbon streams are liquid under normal conditions or can readily be made so, ordinary distillation techniques can be used to separate the hydrocarbon components providing they have sufficiently different boiling points for the process to be economically feasible. Especially when the hydrocarbon mixtures contain materials having close boiling points, which is frequently the case with hydrocarbons of the same number of carbon atoms or having a difference of only one carbon atom, distillation may not be an attractive separation procedure. In such cases, more expensive processes are often used and involve operations such as solvent extraction or extractive distillation which entail considerable expense, if indeed they are technically feasible in a given situation.

When the mixture containing the aliphatically-unsaturated hydrocarbon is essentially in a gaseous state at normal or ambient conditions of temperature and pressure, separation of the desired component from the mixture may be even more troublesome. In these situations, cryogenic processes may be used, but they are expensive. The components of these normally gaseous mixtures may not even have particularly close boiling points, but, nevertheless, the mixture must be cooled in order to separate one or more of its components. In spite of the considerable cost of cryogenic operations, the procedure has been employed commercially for the separation of ethylene from other gaseous materials such as ethane and methane.

We have previously devised methods for separating materials, e.g. aliphatically-unsaturated hydrocarbons, from mixtures containing them, and these procedures involve the combined use of liquid barrier permeation and metal complexing techniques which can exhibit high selectivity factors. In the processes, the liquid barrier is an aqueous solution containing metal ions which will complex with the material to be separated, and the liquid barrier is employed in conjunction with a semi-permeable membrane which is essentially impermeable to the passage of liquid. The present invention is concerned with the manufacture of semi-permeable membranes which can be used in systems of this type in which the liquid barrier containing the complex-forming metal ions is at least partially within a hydrophilic, semi-permeable film membrane. When operating in this manner, there is no need to maintain contact of the film with a separate or contiguous aqueous liquid phase during the process, thereby facilitating the use of a greater variety of semi-permeable members as far as physical configuration is concerned. Thus, the membranes can be designed without the hindrance of having to provide a separate liquid phase adjacent the film, and this may enable the use of film configurations having a greater surface or contact area.

There is a desire in these separating procedures to increase the rate of transport across the semi-permeable film of the material to be separated. An increase in the transport rate will permit the separation of larger amounts of product with a film of given surface area. The increase in rate must not, however, be accompanied by excessive loss in the selectivity of the film towards the desired separation, and it is most advantageous that there be essentially no loss in the selectivity of the separation. These goals can be reached by using semi-permeable films prepared in accordance with the present invention.

The films made and employed in this invention can be formed from solutions containing solvents having dissolved therein the film-forming material and a separate pore-forming material. The pore-forming material is soluble in a solvent in which the resulting film is relatively insoluble. The film is formed from the solution accompanied by the evaporation of solvent to provide an essentially solid film containing the pore-forming ingredient. The film can then be contacted with a solvent which dissolves the pore-forming material from the film without unduly dissolving the film derived from the film-forming material. In this manner, we have obtained films which are still essentially semi-permeable, but which exhibit increased transport rates when used to separate materials by the liquid barrier-complex-forming metal technique. Apparently, the films have more pores than similar films prepared without employing the pore-forming ingredient. The films exhibit increased permeability to vapors or gases, but yet the porosity of the films is not increased to the point that liquids physically pass through the films to any material extent. The resulting films thus retain their semi-permeability and are eminently suitable for use in the selective separation process.

In making the films of this invention, the solvent for the film-forming and pore-forming materials may be organic, inorganic, or mixed solvents of these types, although aqueous media which contain at least a significant amount of water are preferred. The pore-forming ingredient must dissolve in the solvent medium, and thus the pore-forming ingredient will be selected in accordance with the composition of the solvent. We prefer to employ pore-forming materials having molecular weights not exceeding about 1000. The vapor pressure of these materials should not be so great that they are unduly lost from the film by volatilization as it is being formed.

The pore-forming materials may be water-soluble, water-insoluble, organic solvent-soluble, organic solvent-insoluble or exhibit some combination of such properties, depending on the nature of the solvent. In any event, the pore-forming ingredient exhibits a solubility which is significantly different from that of the film derived from the film-forming material in the solvent. This permits removal of the pore-forming material from the film without undue deterioration of the film. Thus, the film is contacted with a liquid solvent for the pore-forming material which solvent is essentially a non-solvent for the film. The resulting film is semi-permeable and exhibits an enhanced transport rate when used in liquid barrier-complex forming metal selective separation procedures.

Among the water-soluble, pore-forming agents are acids and bases, as well as neutral materials. It is preferred that these ingredients be organic. The materials can be removed from the film by washing the film with a liquid aqueous medium in which the film is not soluble to a significant extent. The removal of acids may be enhanced by treatment of the film with a basic washing medium and, conversely, the removal from the film of basic materials may be improved by contact with an acidic medium. Among such pore-forming agents are the water-soluble amines, such as ethylene diamine, diethylamine, pyridine, cyclohexylamine, aniline, hexamethylenetetraamine and the like, and carboxylic acids, e.g. acetic acid, citric acid and the like. Salts of the acids may also serve as the pore-forming material.

Among the pore-forming materials we may use are agents which are organic solvent-soluble. In such cases, the film-forming material and the pore-forming agent are dissolved in a suitable organic solvent. The film is formed from the solution accompanied by evaporation of the solvent, and the resultant film is contacted with an organic solvent which dissolves the pore-forming material but not the film. Among the organic pore-forming materials which may be used are hydrocarbon solids, e.g. waxes, and hydrocarbon liquids having a boiling point of at least about 300° F. These materials can be removed from the films by contact with a solvent, e.g. a lower boiling hydrocarbon liquid such as naphtha, providing the films are not significantly soluble in the solvent.

The amounts of film-forming material and pore-forming agent present in the solution used to make the films may vary considerable. There must be sufficient of the film-forming material in the solution to enable the formation of an essentially solid, semi-permeable, continuous film of sufficient strength to be successfully used in the separation process. The amounts of pore-forming material in the solution and in the film are sufficient so that when removed at least in part from the film, the latter has a significantly improved transport rate when employed in the separation process. At the same time, the amount of pore-forming agent removed from the film must not be so great that the essential semi-permeability of the film is materially lost. Preferably, the amount of film-forming material in the solvent exceeds the amount of pore-forming material present, and thus the latter may be a minor weight amount of the total of these materials on a non-solvent basis, but this may not always be the case. The weight ratio of film-forming material to pore-forming material in the solvent is often about 10 to 1000:1, preferably about 50 to 200:1. The amount of solvent is sufficient to dissolve the other ingredients in the desired amounts and provide a solution of suitable viscosity for forming the film. Often, the amount of solvent used in about 30 to 95 weight percent based on the film-forming material, preferably about 40 to 60 weight percent.

The hydrophilic film membranes of this invention are fairly stable, have satisfactory permeability and exhibit good selectivity for separating materials, for instance, aliphatically-unsaturated hydrocarbons, from mixtures after removal of the pore-forming material from the film. Apparently, the removal of the pore-forming material serves to give a film of an enhanced or increased number of pores. Since the semipermeable nature of the film is not destroyed, these pores apparently do not pass through the film, or, if they do, they are so small that there is still no material increase in the amount of liquid that passes through or from the film during the separation process. It, therefore, seems that the increase in pores in the film is in surface pores, rather than as holes through the film. Thus, by the method of the present invention, we can enhance the transport properties of the film without materially decreasing its semi-permeable and selective separation characteristics.

In the present invention, the metals in the film or in the liquid barrier solution, which metals may serve in the form of metal-containing cations to separate a component from a mixture through the formation of metal complexes of desired properties, include, for instance, the transition metals of the Periodic Chart of Elements having atomic numbers above 20. Included in these metals are those of the first transition series having atomic numbers from 21 to 29, such as chromium, copper, especially the cuprous ion, manganese and the iron group metals, e.g., nickel and iron. Others of the useful complex-forming metals are in the second and third transition series, i.e., having atomic numbers from 39 to 47 or 57 to 79, as well as mercury, particularly as the mercurous ion. Thus, we may employ noble metals such as silver, gold and the platinum group, among which are platinum, palladium, rhodium, ruthenium and osmium. The useful base metals of the second and third transition series include, for example, molybdenum, tungsten, rhenium and the like. Various combinations of these complex-forming metals may also be employed in this invention, either in the presence or absence of other non-metal or non-complexing metal components.

The metal is provided in the film or in aqueous liquid barrier of the separation system in a form which is soluble in this liquid. Thus, the various water-soluble salts of these metals can be used such as the nitrates and halides, for instance, the bromides and chlorides, fluoborates, fluosilicates, acetates, carbonyl halides or other salts of these metals which can serve to form the desired water-soluble complexes when the film is in contact with water. The metal salts should not react with any components of the chemical feedstock used in the separation procedure to form an insoluble material which could block the film membrane or otherwise prevent the separation of a component from the feedstock. Also, in a given system, the metal is selected so that the complex will readily form, and yet be sufficiently unstable, so that the complex will decompose and the dissociated material leave the liquid barrier, thereby providing a greater concentration of the material to be separated from the exit side of the membrane than is in the feed. The concentration of the metal ions in the film or liquid barrier may be rather low and still be sufficient to provide an adequate complexing rate so that excessive amounts of the semi-permeable membrane surface will not be needed to perform the desired separation. Conveniently, the concentration of the complex-forming metal ions in the aqueous solution forming the liquid barrier is at least about 0.1 molar and is preferably about 0.5 to 12 molar. Advantageously, the solution is less than saturated with respect to the complex-forming metal ions to insure that essentially all of the metal stays in solution, thereby avoiding any tendency to plug the film membrane and destroy its permeability characteristics.

When the complexing ions in the liquid barrier employed in this invention include cuprous ions, ammonium ions can be used to provide copper ammonium complex ions which are active to form a complex with the material to be separated by the use of the film. We preferably supply about equimolar amounts of cuprous and ammonium ions, although either type of ions may be in excess. The ammonium ions can be provided in various convenient ways, preferably as an acid salt such as ammonium chloride or as ammonium hydroxide or ammonium carbonate. In order to enhance the selectivity of the copper ammonium ion complex in the separation of this invention, we may also make the film and thus the liquid barrier solution more acidic, by, for instance, providing a water-soluble acid such as a mineral acid, especially hydrochloric acid in the film or liquid barrier solution. Preferably, the pH of the liquid barrier in this form of the invention is below about 5 with the acid in the solution. Since silver may form undesirable acetylides with acetylenes, the copper ammonium complex may be a more attractive complexing agent when it is desired to use the film to separate acetylenes from various mixtures.

Instead of supplying only a noble metal for complexing the material to be separated in the process of this invention, we may also employ mixtures of noble metal and other cation-providing materials. A portion of the noble metal may be replaced by non-noble metal or ammonium components. Accordingly, the total of such ion-forming materials in the film or in the liquid barrier may be composed of a minor or major amount of either the noble metal or the non-noble metal, ammonium or other components. Solutions having a major amount of the non-noble metal, ammonium or other cation-providing materials not containing a noble metal will generally be less expensive, and, accordingly, the noble metal may be as little as about 10 molar percent or less of the total cation-providing material in the solution. To reduce expenses, at least about 10 molar percent, preferably at least about 50 molar percent, on a cation basis of the total, of a cation-providing material may be other than noble metal. The non-noble or base metals are preferably of Groups II to VIII of the Periodic Chart of Elements, and especially those in the fourth and fifth periods, aluminum and magnesium. Zinc and cupric ions are preferred ones among these non-noble or base metal components. The various metals may be provided in the liquid barrier in the form of any suitable compounds, such as the acid salt forms mentioned above with respect to the noble metals.

The amount of water in the liquid barrier employed in this invention may be a minor portion of the liquid phase, but preferably is a major portion or even essentially all of the liquid, on a metal salt-free basis. Thus, small or minor amounts of water, say as little as about 5 weight percent, on a salt-free basis in the liquid phase may serve to provide significant transport for the material to be separated across the liquid barrier. Any other liquid present in the barrier is preferably water-miscible and should be chosen as not to have a substantial deleterious effect on the separation to be accomplished. The liquid barrier may also contain a hygroscopic agent, e.g., in a minor amount, to improve the wetting or hydrophilic properties of the liquid and provide better contact with the feed gas.

In the system of the present invention, the amount of complex-forming metal in the semi-permeable membrane may vary considerably, but is sufficient to accomplish the desired separation. Often, this is a minor amount, say, about 1 to 50 weight percent, of the weight of the membrane on a non-aqueous basis, preferably about 5 to 25 weight percent. A suitable procedure for placing the solution of complex-forming metal in the semi-permeable film is by contacting the film with the solution and exerting a differential pressure across the solution and film. Thus, the pressure behind the solution is greater than that on the opposite side of the film, and as a result, the solution is forced into the film under pressure. Conveniently, the pressure on the solution is above atmospheric, and the opposite side of the film is essentially at atmospheric pressure. The pressure differential need not be large, for instance, it may only be at least about 5 or 10 psi, and it should not be so great that the film is ruptured. This procedure could also be used to reactivate films which have been used to the extent that they have lost selectivity.

The membrane containing the complex-forming metal may be handled and transported in a more or less non-aqueous form or with some water therein, for instance, an insufficient amount of water to be effective in the separation. In such case, water would be added to the membrane to give a film bearing sufficient water to be useful in performing the separation process of the invention. During use of the membrane, the amount of water present is preferably less than that which gives a substantial distinct or separate aqueous phase on the feed inlet side of the membrane. The film membrane can be wetted initially, and if it has a tendency to dry during use, additional water can be placed in the film while it is used on-stream in the separation, for instance, by inclusion of moisture in the gaseous feed charged to the system. Alternatively, but less advantageously, the operation can be stopped for addition of water to the film. The water could be added at intervals by stopping the feeding of the gaseous mixture to the system, and charging water to the membrane at such times. In any event, care should be taken to insure that the film membrane during use is not so dry that it will exhibit non-selective permeability to the material to be separated from the feed, and will thereby not serve to separate a product having an increased concentration of the desired ingredient.

The film membranes employed in the process of this invention can be of the essentially water-insoluble, hydrophilic, semi-permeable type. In the absence in the film of the liquid containing the complex-forming ions, the film is generally not adequately selective with respect to the passage of or permeation by the material to be separated to perform the desired separation at the desired rate. Often, the film is permeable to essentially all of the components in the gaseous feedstock used in this inventin. However, by having the film contain sufficient aqueous liquid to form a barrier, the simple diffusion of gas through the film is reduced or prevented, and the components of the feed stream must, therefore, traverse the film primarily by becoming part of, and then being separated from, the aqueous liquid phase contained in the film. Thus, in the absence of the complexing metal ion in the aqueous medium, there could be a slight separation effected by the use of water as the liquid medium since the individual components in the gas may exhibit differing solubilities in water. In the method of the present invention, however, the selectivity of the separation is greatly increased due to the presence of the complex-forming metal ions in the aqueous barrier medium. Also, during use in the process of this invention, the film has sufficient of the aqueous medium so that adequate metal ions are in solution, or at least react as if they are, to perform the desired separation.

The film membranes which can be employed in this invention are preferably self-supporting and have sufficient strength not to require any additional supporting material on either of its sides during use. With some films, however, it may be necessary, advantageous or convenient to provide adequate support such as additional film or sheet-like materials on one or both sides of the film membrane. These supporting structures are frequently very thin materials and may be permeable to both liquids and gases and not serve as separating function with respect to any component of the feed stream. Alternatively, the supporting film may be permeable to gases, but not to liquids.

The film membrane used in this invention is sufficiently hydrophilic to hold the liquid barrier solution at least partly within the membrane. This hydrophilic property may be present in the film membrane due to the character of the polymer forming the film or due to the presence of additives such as hygroscopic agents in the film which contribute to the hydrophilic nature of the composite. Both the polymer and additive may contribute hydrophilic properties, and a combination of a hydrophilic film and a hygroscopic agent may be advantageously employed. The film membrane may be considered sufficiently hydrophilic to be used in the present invention if it absorbs at least about 5 weight percent of water when immersed in distilled water for one day at room temperature and pressure.

Suitable film membranes for use in this invention include those which are in essence polymer gels, including hydrogels. These polymer gels are exemplified by gels of the polyurethane type. Thus, we may react essentially hydrocarbon polyisocyanates, especially predominantly diisocyanate materials, with an aliphatic polyol, and preferably, the latter has more than two hydroxyl groups per average molecule so that the polymer film is cross-linked sufficiently to give a membrane of adequate strength. The polyisocyanates often have about 4 to 20, preferably about 6 to 12, carbon atoms per molecule, and may be aliphatic, including cycloaliphatic, aromatic or mixed structures of these types. The polyol is preferably, but not necessarily, water-soluble, and often the polyol may have a molecular weight of at least about 100. Suitable polyols include the polyvinyl alcohols, polyoxyethylene alcohol ethers, cellulose and its hydroxyl-containing derivatives and hydroxylated polymethacrylates and polyacrylates. If desired, in making the polyurethanes, the polyisocyanate and polyol may be reacted in approximately stoichiometric amounts; however, either reactant may be in excess, especially the polyol, since free polyol remaining may serve as a hygroscopic agent.

The film membrane may be in any useful physical shape. Flat film sheet is one form, although greater surface areas and more efficient separation may be provided by using tubular fibers of the types disclosed in, for instance, U.S. Pat. No. 3,228,877, herein incorporated by reference. This patent described a variety of hydrophobic or hydrophilic hollow fibers which may be employed in the present invention. The more hydrophobic films may be made more hydrophilic by the incorporation of materials which increase the affinity of the films for water. The useful membranes include, for example, those of cellulose acetate, polyesters, nylon, polyvinyl chlorides, polyvinyl alcohols, polyvinyl acetate, polystyrene, cation-exchange resins such as divinylbenzene cross-linked, sulfonated polystyrenes, olefin polymers such as polyethylene, polypropylene and ethylene-propylene copolymers, polyurethanes, ethylene-vinyl acetate copolymers, ethylene-ethyl acrylate copolymers, silicone elastomers and the like. Other suitable membranes are described in "Gas Permeability of Plastics," Major et al., *Modern Plastics,* page 135 et. seq., July, 1962; and U.S. Pat. Nos. 3,133,132; 3,133,137; 3,256,675; 3,274,750; 3,325,330; 3,335,545; 3,396,510 and 3,447,286, all incorporated herein by reference. The film membranes may often have a thickness up to about 30 mils or more, and we prefer to employ membranes having a thickness up to about 10 mils. The films must have sufficient thickness to avoid rupture at the pressures employed, and often, the films may have a thickness of at least about 0.001 mil.

Among the film-forming materials which can be employed to provide the semi-permeable film membranes used in the present invention, we prefer those having a polyamide as an essential component. The polyamide film-forming materials are generally known and have also been designated as nylons. The polymers are characterized by having a plurality of amide groups serving as recurring linkages between carbon chains in the product structure, and the polymers may be made by several procedures. Commonly, the polyamides are formed by reacting a polyamine and a dicarboxylic acid or its derivative such as an ester, especially a lower alkyl ester having, for instance, about 1 to 4 carbon atoms in each ester group. Other reactions which may be employed to form the polyamides include the self-condensation of monoamino, monocarboxylic acids and the reactions of cyclic lactams. In any event, the polyamide products contain recurring amide groups as an integral part of the principle polymer chain. The polyamides are described, for instance, in the Kirk-Othmer, *Encyclopedia of Chemical Technology,* Second Edition, Volume 16, beginning at page 1, Interscience Publishers, New York, 1968. Among the typical structural formulas of the linear polyamides are $H_2NRNH(COR'$ $CONHRNH)_nCOR'COOH$ and $H_2NRCO(NHRCO)_nNHRCOOH$, where R and R' represent primarily carbon-to-carbon chains between functional groups in the reactants, and n represents the degree of polymerization or the number of recurring groups in the polymer chain. The polyamides which can be used in this invention are generally solid at room temperature, and have a molecular weight which makes them suitable for forming the desired film membranes. Polyamides of this type are described in, for instance, U.S. Pat. No. 3,355,409.

The carboxylic acids which may be used in forming the polyamides have an acyloxy group (—R—COO—) in their structure and the R member of this group is composed essentially of carbon and hydrogen and often contains about 6 to 12 carbon atoms. Such groups may be aliphatic, including cycloaliphatic, aromatic, or a mixed structure of such types, but such groups are preferably aliphatic and saturated with respect to carbon-to-carbon linkages. These R groups may preferably have straight chain carbon-to-carbon or normal structures. Among the useful dicarboxylic acid reactants are adipic acid, sebacic acid, azelaic acid, isophthalic acid, terephthalic acid, and the methyl esters of these acids.

The polyamines employed in making the polyamide film-forming membranes generally have at least two non-tertiary, amino nitrogen atoms. These nitrogen atoms may be primary or secondary in configuration, although amines having at least two primary nitrogen atoms are preferred. The polyamines may also have both primary and secondary nitrogen atoms and the polyamines may contain tertiary nitrogen atoms. The preferred polyamine reactants have aliphatic, including cycloaliphatic, structures, and often have from 2 to about 12 carbon atoms. Also, the preferred polyamines are saturated and have straight-chain structures, although branched-chain polyamines can be used. Among the useful polyamines are ethylene diamine, pentamethylene diamine, hexamethylene diamine, diethylene triamine, decamethylene diamine and their N-alkyl substituted derivatives, for instance, the lower alkyl derivatives which may have, for instance, 1 to 4 carbon atoms in each alkyl substituent.

Film-forming polyamides which can be employed in this invention include those in which the polyamide is an N-alkoxyalkyl-substituted polyamide. Materials of this type are well known, as shown, for instance, by U.S. Pat. Nos. 2,430,910, and 2,430,923, which disclose N-alkoxymethyl polyamides made by the reaction of a polyamide polymer, formaldehyde and alcohol. Generally, at least about 5% of the amide groups of the polymer are substituted with the alkoxyalkyl group and such substitution may be up to about 60% or more. Preferably, this substitution is about 10 to 50% and the product is soluble in hot ethanol.

The alcohols employed in making the N-alkoxyalkyl polyamides are generally monohydric and may have, for instance, from 1 to about 18 or more carbon atoms. The lower alkanols are preferred reactants, especially the lower alkanols having 1 to 4 carbon atoms. Among the useful alcohols are methanol, propanols, butanols, oleyl alcohol, benzyl alcohol, lauryl alcohol and alcohol ethers, for instance, the alkyl ethers of ethylene glycol.

The N-alkoxyalkyl polyamides which can be employed as film-forming materials in the present invention to provide the desired semi-permeable membrane may be reacted with cross-linking agents. Such agents may be, for example, polycarboxylic acids, especially the dicarboxylic acids which may have, for instance, from 2 to about 12 carbon atoms. Useful cross-linking acids include oxalic acid, citric acid, maleic acid, and the like.

The metal-containing, semi-permeable films made by the procedure of the present invention may be employed, for instance, to separate one or more unsaturated hydrocarbons by the liquid barrier-complex-forming technique having the barrier at least partly, and preferably essentially entirely, within the film. Although the products thus separated may be quite pure materials, for instance, of greater than 99% purity, the separation procedure may be used merely to provide a significant increase in the concentration of a given material in a mixture with other components of the feedstock.

The process can be employed to separate various materials from other ingredients of the feed mixture providing at least one of the components of the feed exhibits a complexing rate or transfer rate across the liquid barrier in the film that is greater than at least one other dissimilar or different component of the feedstock. Quite advantageously, the system can be used to separate aliphatically-unsaturated hydrocarbons from other hydrocarbons which may be aliphatically saturated or aliphatically-unsaturated, or from non-hydrocarbon materials, including fixed gases such as hydrogen. The feed mixture may thus contain one or more paraffins, including cycloparaffins, mono- or polyolefins, which may be cyclic or acyclic, and acetylenes or alkynes, and the mixture may include aromatics having such aliphatic configurations in a portion of their structure. Often, the feed mixture contains one or more other hydrocarbons having the same number of carbon atoms as the unsaturated hydrocarbon to be separated or only a one carbon atom difference. Among the materials which may be separated according to this invention are ethylene, propylene, butenes, butadiene, isoprene, acetylene and the like.

In the method, the mixture containing the material to be separated may be essentially in the gaseous or vapor phase when in contact with the liquid barrier having dissolved therein one or more metal ions which form a complex with the material to be separated. The liquid barrier is in contact with the semi-permeable membrane which may be permeable to the feed mixture in the absence of the liquid barrier. The membrane can be said to immobilize the liquid barrier within the membrane. The liquid barrier may in essence be completely within the semi-permeable structure, and the liquid does not pass from the membrane to an excessive extent under the conditions of operation. The membrane is, however, selectively permeable in the presence of the liquid barrier to the component of the feedstock to be separated. Since there is little, if any, passage for the feedstock across the separation zone except by becoming part of or reacting with the liquid barrier, the liquid barrier controls the selectivity of the liquid barrier-semi-permeable membrane combination.

The liquid barrier contains sufficient water and soluble metal ions to form a suitable complex with at least one component of the feed subjected to the separation procedure. The metal ions readily form the complex upon contact with the feed, and, in addition, the complex dissociates back to the metal ion and the feed component of the complex, under the conditions which exist on the discharge side of the liquid barrier and semi-permeable membrane as employed in the process. The released feed component exits the discharge side of the membrane and can be removed from the vicinity of the barrier and its supporting structure as by a sweep gas or through the effect of vacuum on this side of the barrier. Thus, the metal complex forms and is decomposed in the complex metal ion-containing liquid barrier, and, as a result, the material passing through the barrier is more concentrated with respect to at least one component present in the feed stream.

Often, the reactivity of aliphatically-unsaturated hydrocarbons with the complexing metal ions in their order of decreasing activity goes from acetylenes or dienes to monoolefins, the aliphatically-saturated hydrocarbons and other materials present being essentially non-reactive. Also, different reactivities may be exhibited among the various members of a given type of aliphatically-unsaturated hydrocarbons. The process can thus be used to separate paraffins from monoolefins, diolefins or acetylenes; diolefins from monoolefins; or acetylenes from paraffins, monoolefins or diolefins; as well as to separate a given aliphatically-unsaturated hydrocarbon from another of such materials in its class where the members have differing complexing rates with or transport rates across the liquid barrier. The feed need only contain a small amount of aliphatically-unsaturated hydrocarbon, as long as the amount is sufficient so that the unsaturated material to be separated selectively reacts with the metal complex ions to a significant extent, and thus at least one other component of the feed is less eactive or non-reactive with the complex-forming metal ions.

The aliphatically-unsaturated materials of most interest with regard to separation have 2 to about 8 carbon atoms, preferably 2 to 4 carbon atoms. The separation of aliphatically-unsaturated materials from admixtures containing other gaseous materials, such as the separation of ethylene or propylene from admixtures with other normally gaseous materials, e.g. one or more of ethane, propane, and methane and hydrogen, is of particular importance. Frequently, such feed mixtures for the process contain about 1 to 50 weight percent ethylene, about 0 to 50 weight percent ethane and about 0 to 50 weight percent methane. Another process that may be of special significance is the separation from ethylene of minor amounts of acetylene.

The component of the feed to be separated has a partial pressure at the input side of the liquid barrier used in the separation, greater than the partial pressure of this component on the discharge or exit side of the liquid barrier-semi-permeable membrane composite. This pressure drop of the component to be separated may often be at least about 0.5 pound per square inch, and is preferably at least about 20 p.s.i., although the pressure drop should not be so great that the liquid barrier is ruptured or otherwise deleteriously affected to a significant extent. Conveniently, the total pressure of the feed is up to about 1000 pounds per square inch. The discharge partial pressure of the separated component can preferably be controlled by subjecting the exit side of the liquid barrier to the action of a sweep gas that may be essentially inert to forming a complex with the metal ions in solution in the liquid barrier. The sweep gas picks up the discharged component, and the sweep gas may be selected so that it can be readily separated from the product if that be necessary for its subsequent use. Unless a reaction with the separated feed component is desired, the sweep gas should be relatively inert therewith and may be, for instance, butane, carbon dioxide or the like.

The temperature across the liquid barrier-semi-permeable film composite employed in the separation procedure can be essentially constant or it may vary, and decomposition of the metal complex can be affected primarily by the drop in partial pressure of the separated component on the exit side of the liquid barrier compared with the partial pressure on the feed side. Conveniently, the temperature of the liquid barrier may be essentially ambient, especially in the case of feedstocks that are gaseous at this temperature and the pressure employed on the feed side of the liquid barrier. The temperature of the liquid barrier may, however, be reduced or elevated from ambient temperature. Often, the temperature may be up to about 100° C., and elevated temperatures may even be desired to put the feedstock in the gaseous or vapor phase. Neither the temperature nor the pressure used should, however, be such as to destroy the difference in transport rate across the liquid barrier, semi-permeable film composite of the material whose separation is sought, compared with that of the other components of the feed. The conditions should also not be such that physical disruption of the liquid barrier or any other significant malfunction results.

The present invention will be further illustrated by the following specific examples.

A series of nylon films containing a water-soluble, pore-forming agent was prepared. The films were cast from a methanol solution containing 20 weight percent of a commercially-available nylon, DuPont's Elvamide 8061, melting point, 315° F. (ASTM-D789), and varying amounts of citric acid as a pore-forming material. The films had a thickness of 1.2 mils. The cast films were immersed in water and allowed to stand therein for at least 2 hours to leach out the citric acid. The films were then removed from the water and allowed to air dry.

The permeability of the films to ethylene was measured in a cell which was divided into upper and lower compartments by locating the film horizontally across the cell. The cell internal cross-sectional area was 4.9 cm.$^2$ and the cross-section was fully covered by the film membrane in a manner to provide an effective membrane area of 2.2 cm.$^2$ The main body of the cell has a height of 22 mm. and a gas outlet at each end. A feed inlet tube entered the upper end of the cell and opened about 5 mm. above the film, and a sweep gas inlet tube entered the lower end of the cell and opened about 4 mm. below the film. A hydrocarbon feed (19.20% $CH_4$, 50.29% $C_2H_4$, 30.51% $C_2H_6$) was charged under a pressure of 30 psig. into the upper portion of the cell at the rate of 10 ml./min. and into contact with the membrane, and the exhaust or raffinate components of the gas left the cell by the upper outlet. The feed rate was considered to be sufficient to maintain a constant gas composition on the inlet side of the membrane. A sweep gas (10 ml./min. of helium) contacted the lower surface of the membrane, picked-up the material permeating the membrane, and then exited the cell by the lower outlet as a product stream. The product was analyzed by gas chromatography with the helium serving as the carrier gas. The tests were at ambient temperature.

The permeation rates of several films made as described above, but containing differing amounts of pore-forming material in the casting solution, were determined. The tests were made in the cell and in the manner described above. The results are shown in the following table.

TABLE I

| Film No. | Porosity[1] (%) | Permeation Rate[2] (ml/cm²-min) |
|---|---|---|
| 1 | 0 | 0.0000236 |
| 2 | 20 | 0.00092 |
| 3 | 25 | 0.00785 |
| 4 | 30 | 0.0339 |
| 5 | 40 | 0.185 |
| 6 | 50 | 0.385 |

[1]Measured as amount of pore-forming material relative to amount of polymer in the casting solution.

$$\text{Porosity} = \frac{\text{Wt. of Citric Acid}}{\text{Wt. of Nylon}} \times 100$$

[2]Recorded at a feed pressure of 30 psig and represents only the ethylene permeation rate.

These data show that permeability of the films increased as the amount of pore-forming agent in the casting solution increased.

To illustrate the utility of films of increased permeability as reported in Table I, they were employed to separate ethylene from a humidified mixed hydrocarbon stream. The films were impregnated with silver ions by soaking the films overnight in a solution of 6 M AgNO$_3$ in aqueous 5% polyvinyl alcohol, the latter having a molecular weight of 1820 and serving as a hygroscopic agent. The silver-containing films were then used to separate ethylene in accordance with the procedure described above for determining film permeability, except that the feed pressure was 10 psig. The results of this work are reported in Table II.

TABLE II

| Film No. | P$_2$[1] (ml/cm²-min) | Permeate Composition (wt%) | | | S[2] |
|---|---|---|---|---|---|
| | | Methane | Ethylene | Ethane | |
| — (Feed | — | 19.20 | 50.29 | 30.51) | — |
| 2 | 0.0089 | 0.4 | 99.3 | 0.3 | 212 |
| 3 | 0.0092 | 0.2 | 99.7 | 0.1 | 393 |
| 5 | 0.0425 | 0.13 | 99.80 | 0.07 | 541 |

[1]Measured at 10 psi and represents only ethylene permeation rate.

$$^2S = \frac{[\text{Ethylene}]\text{Permeate}}{[\text{Methane} + \text{Ethane}]\text{Permeate}} \times \frac{[\text{Methane} + \text{Ethane}]\text{Feed}}{[\text{Ethylene}]\text{Feed}}$$

The permeation rates reported in Table II differ slightly from those in Table I because the films reported on in Table I contained no complex-forming metal and were dry. Also, the permeation rates given in both tables represent only the ethylene that was permeated. With the dry films of Table I, no separation selectivity was observed, and thus the total permeation would be significantly increased by the amounts of methane and ethane which also passed through the film. When using the films containing the complex-forming metal ions as reported in Table II, the amounts of methane and ethane which permeated the films are insignificant. The data of Table II show not only an increased ethylene permeation rate, but also a high selectivity for the separation of ethylene when using films made in accordance with the present invention.

It is claimed:

1. A method of making a semi-permeable, essentially water-insoluble, hydrophilic, nylon film membrane which is essentially impermeable to liquids and wherein the membrane is suitable for separating aliphatically-unsaturated hydrocarbons of 2 to 4 carbon atoms from mixtures containing them, which comprises forming the film membrane from a solvent solution of film-forming viscosity having dissolved in a solvent hydrophilic, nylon film-forming material and citric acid pore-forming material, said pore-forming material being provided in a minor amount sufficient to increase the porosity of the nylon film when removed from the film, removing the solvent by evaporation thereby providing an essentially solid, nylon film containing citric acid pore-forming material, contacting the nylon film with an aqueous solvent for the pore-forming material, said nylon film being essentially insoluble in said solvent, to dissolve at least a portion of the pore-forming material from the nylon film sufficient to increase the porosity of the nylon film, and incorporating in the film metal containing ions which form a water-soluble complexes with said aliphatically-unsaturated hydrocarbons of 2 to 4 carbon atoms, to provide a porous, hydrophilic nylon film membrane which is essentially impermeable to liquids.

2. The method of claim 1 wherein the metal is noble metal.

3. The method of claim 2 wherein the metal is silver.

4. The method of claim 1 wherein the weight ratio of film-forming material to pore-forming material is about 10 to 1000:1.

5. The method of claim 1 wherein the amount of pore-forming material is 20 to 50 percent based on the amount of hydrophilic, film-forming material in the solvent solution.

6. An essentially water-insoluble, hydrophilic semi-permeable polymer film made by the process of claim 1.

7. The film of claim 6 wherein the metal is noble metal.

8. The film of claim 7 wherein the metal is silver.

* * * * *